United States Patent
Abrahamson et al.

(10) Patent No.: US 8,868,200 B2
(45) Date of Patent: Oct. 21, 2014

(54) IMPLANTABLE MEDICAL DEVICE WITH AN IMPROVED ANTENNA

(75) Inventors: Hans Abrahamson, Stockholm (SE); Viktor Skoog, Hässelby (SE)

(73) Assignee: St. Jude Medical AB, Jarfalla (SE)

( * ) Notice: Subject to any disclaimer, the term of this patent is extended or adjusted under 35 U.S.C. 154(b) by 710 days.

(21) Appl. No.: 13/125,518

(22) PCT Filed: Oct. 29, 2008

(86) PCT No.: PCT/SE2008/000615
§ 371 (c)(1),
(2), (4) Date: Apr. 21, 2011

(87) PCT Pub. No.: WO2010/050852
PCT Pub. Date: May 6, 2011

(65) Prior Publication Data
US 2011/0196453 A1     Aug. 11, 2011

(51) Int. Cl.
*A61N 1/00* (2006.01)
*A61N 1/372* (2006.01)
*A61N 1/39* (2006.01)
*A61N 1/362* (2006.01)

(52) U.S. Cl.
CPC ........... *A61N 1/37229* (2013.01); *A61N 1/3956* (2013.01); *A61N 1/362* (2013.01)
USPC ................................. 607/60; 607/36; 607/37

(58) Field of Classification Search
CPC . A61N 1/27229; A61N 1/362; A61N 1/3956; A61N 1/37229; H01Q 1/36; H01Q 1/38
USPC ........................... 607/37, 32, 36, 60; 343/873
See application file for complete search history.

(56) References Cited

U.S. PATENT DOCUMENTS

| | | | |
|---|---|---|---|
| 6,009,350 | A | 12/1999 | Renken |
| 6,456,256 | B1 * | 9/2002 | Amundson et al. ........... 343/873 |
| 7,047,076 | B1 | 5/2006 | Li et al. |
| 7,317,946 | B2 | 1/2008 | Twetan et al. |
| 7,917,226 | B2 * | 3/2011 | Nghiem et al. ................. 607/60 |
| 2002/0123776 | A1 | 9/2002 | Von Arx et al. |
| 2006/0241724 | A1 | 10/2006 | Dublin et al. |
| 2006/0247711 | A1 | 11/2006 | Verhoef et al. |
| 2006/0247712 | A1 | 11/2006 | Fuller et al. |
| 2007/0288064 | A1 | 12/2007 | Butson et al. |
| 2008/0021522 | A1 * | 1/2008 | Verhoef et al. ................. 607/60 |
| 2009/0228074 | A1 * | 9/2009 | Edgell et al. ..................... 607/60 |
| 2009/0248112 | A1 * | 10/2009 | Mumbru et al. ................ 607/60 |

* cited by examiner

*Primary Examiner* — Mark W Bockelman

(57) ABSTRACT

An implantable medical device has a housing having a first housing surface side, a second housing surface side opposing the first housing surface side, and an intermediate surface side extending between the first and second housing surface sides. The implantable medical device has an antenna device arranged at the first housing surface side, continuing at the intermediate surface side and further at the second housing surface side. Improved radiation characteristics are obtained in a desired direction.

7 Claims, 1 Drawing Sheet

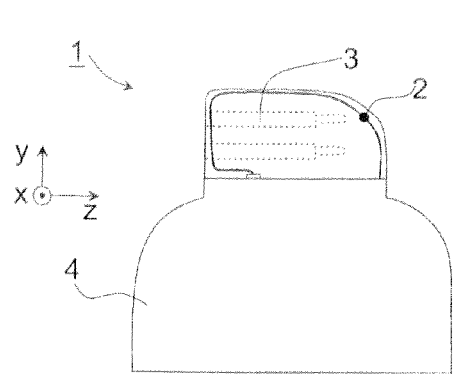
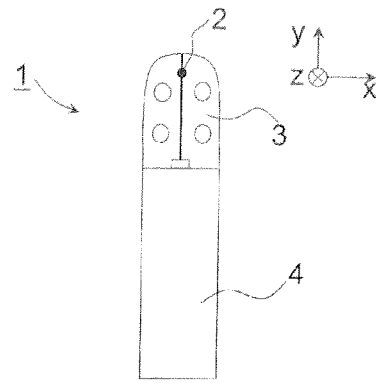
Fig. 1a
Fig. 1b
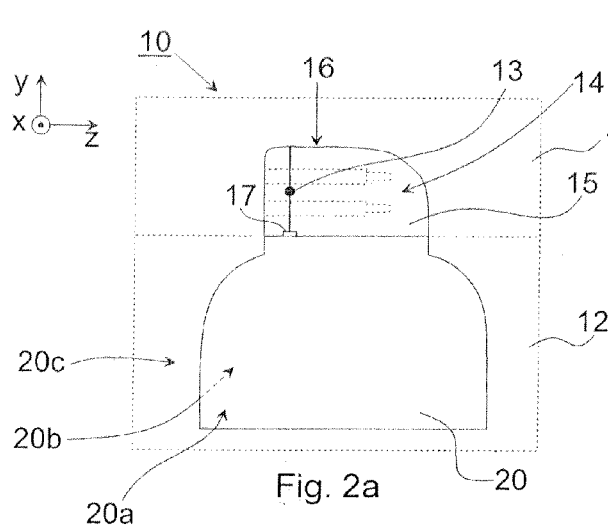
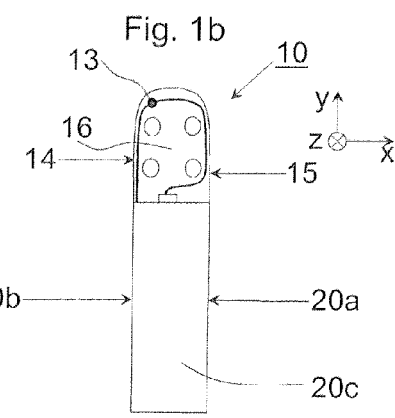
Fig. 2a
Fig. 2b
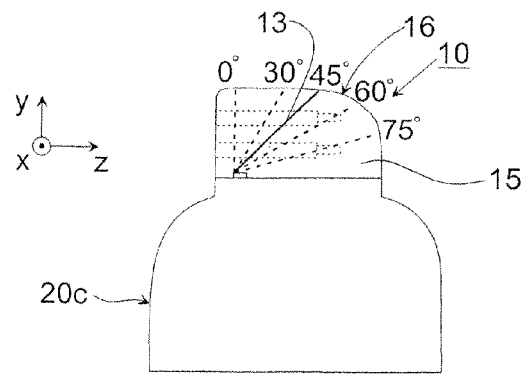
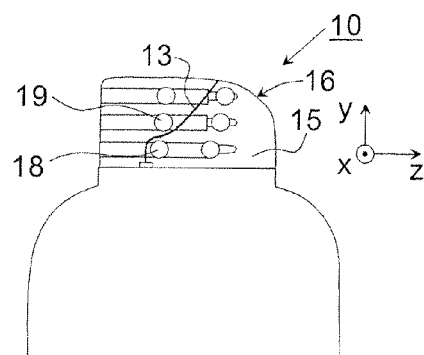
Fig. 3
Fig. 4

IMPLANTABLE MEDICAL DEVICE WITH AN IMPROVED ANTENNA

FIELD OF THE INVENTION

The invention relates to the field of implantable medical devices and in particular to means for wireless communication to/from such implantable medical devices.

DESCRIPTION OF THE PRIOR ART

Implantable medical devices, such as, for example, pacemakers or defibrillators, can be programmed over wireless communication links by means of an external programming device comprising a transceiver. The implantable medical device can thus, when implanted, be programmed by a cardiologist to provide the desired function, for example adjusting the pacing mode of the pacemaker for maintaining a desired heart rate.

The importance of having a reliable communication link between the implantable medical device and the external programming device is readily understood. However, the size of the medical implantable device is rather restricted and limits the size of required communication means, such as antennas.

The ability of the antenna to propagate electromagnetic waves is dependent on the antenna shape and size as well as on the orientation of the antenna. In order to obtain the most favorable radiation characteristics for a closed loop antenna, which is an antenna conventionally used in medical implantable devices, the area encircled by the antenna wire is kept as large as possible. More specifically, the gain of the loop is dependent on the area enclosed by the antenna wire and the loop antenna radiation pattern thus depends largely on the size of the loop.

FIGS. 1a and 1b illustrate in a front view and side view, respectively, such an antenna configuration for an implantable medical device 1. In order to obtain as long circumference as possible for the closed loop antenna, the antenna wire 2 is arranged along a header portion 3 of the implantable medical device 1.

SUMMARY OF THE INVENTION

When communicating over a radio frequency link from the implantable medical device 1 to an external transceiver (not shown in FIGS. 1a and 1b), it is desirable to orientate the antenna of the implantable medical device 1 so as to obtain the most favorable radiation characteristics in a direction in which the communication is most often effectuated. In particular, it would be desirable to maximize the radiated electrical field perpendicular from the body part in which the implantable medical device is implanted, e.g. in the case of a pacemaker it would be most desirable to have the electrical field maximum along an axis normal to the chest of the patient.

In the case of the closed loop antenna illustrated in FIGS. 1a and 1b, the maximum radiation is obtained in the directions perpendicular to the x-axis passing through the centre of the loop. That is, the highest radiation is obtained along the y- and z-axes indicated in FIG. 1a. As the medical implantable device 1 is implanted with its principal flat side, indicated at reference numeral 4, essentially facing the chest of the patient, the highest E-field strength from the antenna 2 is therefore obtained in a direction along the chest of the patient (z-axis), and not perpendicular thereto.

It is an object of the invention to provide an implantable medical device having an antenna configuration providing improved radiation characteristics in a desired direction.

It is another object to provide an implantable medical device having improved overall radiation characteristics, in particular having an overall more uniform performance irrespective of direction relative an external transceiver.

It is yet another object of the invention to provide an implantable medical device, providing a more reliably and easily optimized communication link for users performing medical follow-ups on his/her own.

In accordance with the invention, an implantable medical device has a housing that has a first housing surface side and a second housing surface side opposing the first housing surface side. The housing further has an intermediate surface side that extends between the first and the second housing surface sides. The implantable medical device is characterized by an antenna device arranged at the first housing surface side, continuing at the intermediate surface side and extending further at the second housing surface side. By means of the innovative antenna configuration, more uniform radiation characteristics are obtained in view of the relative orientations between the implantable medical device and an external transceiver device. When data is to be communicated between the implantable medical device and the external transceiver, the user wearing the implantable medical device can more rapidly obtain the required communication link to the external transceiver. This is especially advantageous when performing check-ups or medical follow-ups alone at home, and the user is able to easily see and reach the external transceiver device while the implantable medical device and the external transceiver is in communication with each other.

In accordance with an embodiment of the invention, the housing of the implantable medical device comprises a header portion and the antenna device is arranged entirely at this header portion. Further, the antenna device is, in an embodiment, tilted in relation to a vertical axis of the header portion. A longer antenna element can thereby be used.

BRIEF DESCRIPTION OF THE DRAWINGS

FIGS. 1a and 1b illustrate a known antenna configuration of an implantable medical device.

FIGS. 2a and 2b illustrate in different views an embodiment of the present invention.

FIG. 3 illustrates another embodiment of the present invention.

FIG. 4 illustrates still another embodiment of the present invention.

DESCRIPTION OF THE PREFERRED EMBODIMENTS

The same reference numerals are used throughout FIGS. 2a, 2b, 3, and 4 for denoting same or corresponding parts.

The invention is based on the findings that the antenna configuration having the traditionally oriented antenna that provides the longest possible circumference of the antenna wire is not the most advantageous in all aspects.

Although the circumference of the antenna wire as configured in accordance with the invention, is not necessarily the longest possible, the inventors of the present invention have found that advantages and improved radiation properties may still be obtained by the antenna configuration as presented in the following.

FIGS. 2a and 2b illustrate in a front view and side view, respectively, an embodiment of the present invention. The implantable medical device 10 comprises a header portion 11, also termed connector header, in the figure surrounded by dashed lines in order to define and clearly illustrate the header portion 11 of the implantable medical device 10. The header portion 11 is the part of the implantable medical device 10 containing connection means, for example connection means for electrodes of a pacemaker delivering electrical impulses for regulating the beating of the heart. The header portion 11 is preferably made of a non-conducting material, such as plastics.

The lower part of the implantable medical device 10, containing e.g. batteries and circuitry, is termed main body 12 in the following. In conformity with the above, the main body 12 is illustrated surrounded by dashed lines.

The entire housing of the implantable medical device 10 is indicated in FIG. 2a at reference numeral 20. The housing 20 comprises two opposing major housing surface sides 20a, 20b and an intermediate surface side 20c interconnecting the two major housing surface sides 20a, 20b.

In accordance with the invention, the antenna device 13, or antenna wire, is arranged in an innovative manner. In particular, the antenna device 13 is rotated 90 degrees compared to the prior art antenna configuration illustrated in FIGS. 1a and 1b. The electrical length of the antenna device 13 is therefore not necessarily the longest possible and does therefore not encircle as large area as possible.

With reference to FIGS. 2a and 2b, the header portion 11 comprises two major surfaces, a first and a second major surface 14, 15, being essentially parallel to each other. These first and second major surfaces 14, 15 thus constitute part of the entire housing surface sides 20a, 20b. The first and second major surfaces 14 and 15 are accordingly arranged opposite each other and extend in the y-z-plane, wherein the x-, y- and z-axes are defined as indicated in FIGS. 2a and 2b, respectively. The surface extending between these major surfaces 14, 15 is indicated in the figures at reference numeral 16 and is in the following termed intermediate surface 16. The intermediate surface 16 constitutes part of the entire housing surface side 20c. With reference to FIG. 2a, the intermediate surface 16 extends in the x-y-plane, continues in the x-z-plane and then extends again in the x-y-plane. The intermediate surface 16 can thus be considered as being essentially U-shaped, while the major surfaces 14 and 15 are essentially planar, or slightly vaulted.

The antenna device 13 is arranged from a feeding point 17 of a power source, extending over the first major surface 14, continuing over the intermediate surface 16 and finally extending along the second major surface 15. In the FIGS. 2a and 2b, the antenna is illustrated as extending essentially parallel to the y-axis along the first and second major surfaces 14, 15 and essentially parallel to the x-axis along the intermediate surface 16. The electrical length of the antenna device 13 is thus not the maximum obtainable length. The antenna configuration in accordance with the prior art, wherein the antenna wire is arranged in its entirety along the intermediated surface, would in most cases provide a longer electrical length.

In the above-described embodiment, the antenna device 13 is arranged entirely at the header portion 11. However, in alternative embodiments, the antenna device 13 may be arranged partly on the main body 12 and partly on the header portion 11, taking due consideration to the material of the main body 12 etc.

In another embodiment of the invention, the antenna wire 13 is tilted as illustrated in FIGS. 3 and 4. That is, in contrast to the embodiment of FIGS. 2a, 2b wherein the antenna device 13 is arranged essentially along the y- and x-axes, the antenna device 13 of this embodiment is tilted.

In particular, with reference to FIG. 3, the portions of the antenna device 13 arranged on the major surface 15 is arranged in the y-z-plane and tilted in relation to the y-axis. The antenna wire 13 may be arranged so as to make any suitable angle relative the y-axis within the range of 0 and 90°, for example within the range of 15-60°, and a desirable tilt angle has been found to be about 45°±15°, i.e. within the range of 30°-60° as seen relative the y-axis.

Specifically, in this embodiment the antenna device 13 is arranged tilted along the first major surface 14, extending over the intermediate surface 16 and continuing along the second major surface 15. The antenna device 13 may, but need not, be tilted along the second major surface 15 as well. That is, the antenna device 13 may be symmetrically arranged along the two major surfaces 14, 15, the antenna device 13 thus being mirrored on the major surfaces. On the intermediate surface 16 the antenna device 13 may be arranged essentially along the x-axis, or tilted in relation to the x-axis. That is, the part of the antenna device 13 extending over the intermediate surface 16 may be arranged so as to make an angle to the x-axis in the x-z-plane.

FIG. 4 illustrates the antenna device 13, wherein modifications of the antenna configuration of FIG. 3 have been made in view of practical considerations. Specifically, the antenna wire 13 may need to be arranged slightly deviating from the configuration described above in connection with FIG. 3, due to practical limitations, such as set screws or the like. The antenna device 13 may therefore need to be arranged so as to extend around a set screw 18, i.e. extending on the second major surface 15 along the y-axis a short distance, then extending between two set screws 18, 19 essentially in a direction along the z-axis, before being arranged to make the desired angle to the z-axis.

By tilting the antenna device 13, the antenna wire can be made longer compared to the embodiment as described in connection with FIGS. 2a and 2b.

By the antenna configuration in accordance with the invention, improved radiation characteristics are obtained in a direction perpendicular to the chest of the patient. It is easier for the patient to obtain a reliable communication link, and in particular to align himself, and thereby the implantable medical device, to the external transceiver device for obtaining the most favorable radiation characteristics in the desired direction. This is especially advantageous when performing check-ups or medical follow-ups alone at home. The patient is able to easily see and possibly also reach the external transceiver device while the implantable medical device and the external transceiver is in communication with each other. This since the most favorable radiation characteristics is obtained in the direction perpendicular to the patient's chest.

In the above description, the header is described as comprising connection means. It is noted that the antenna configuration of the present invention can be arranged in a header portion not comprising any such connection means.

It is further to be noted that the antenna device 13 may be a magnetic field antenna, such as the above described closed loop antenna or an electric field antenna with a non-closed antenna structure.

Further, in the above-description, the antenna device 13 is described as being arranged along or at the surface sides 14, 15, 16, 20a-c. It is to be noted that this wording is meant to include antenna elements being arranged on the outside of the housing surface as well as antenna elements being embedded within the housing material.

Further yet, as a definition, a vertical axis of the implantable medical device 10 is to be understood as an axis passing through the housing 10 in a direction that is vertical for the implantable medical device 10 when implanted. The vertical axis thus passes through the both parts of the implantable medical device 10, i.e. both the header portion 11 and the main body 12. Throughout the figures, the vertical axis would be along the y-axis. The horizontal axes are obviously perpendicular to the vertical axis, and passes through the housing 20 in its width extension (x-axis) and in its length extension (z-axis). As a matter of definition, the horizontal axis, as used in the claims, is defined to be along the x-axis. The horizontal axis is essentially parallel to a normal of the chest of a user, in the case of the implantable medical device being a pacemaker.

In summary, by means of the present invention, the innovative antenna configuration of the implantable medical device provides an improved reliability of providing a proper communication link between the implantable medical device and the external transceiver. The quality of the communication link is not as dependent upon the placement of the patient having the implantable medical device in relation to the external transceiver, when compared to the prior art antenna configuration. Differently stated, the communication link is less dependent on the patient being oriented properly in relation to the external transceiver.

The desired radiation characteristics are maintained to a larger extent for the innovative antenna configuration than for the prior art antenna configuration when the implantable medical device is moved in relation to the external transceiver, in particular when it is rotated in relation to the external transceiver. The radiation characteristics are more uniform when considering the relative orientations between the implantable medical device and the external transceiver.

Although modifications and changes may be suggested by those skilled in the art, it is the intention of the inventors to embody within the patent warranted heron all changes and modifications as reasonably and properly come within the scope of their contribution to the art.

We claim as our invention:

1. An implantable medical device comprising:
   a main body;
   a header portion having a first header portion surface side, a second header portion surface side opposite said first header portion surface side, an intermediate surface side extending between said first and second header portion surface sides, and an intermediate base surface side extending between said first and second header portion surface sides and opposite said intermediate surface side, said header portion attached to said main body at said intermediate base surface side; and
   an antenna device having a first portion arranged at said first header portion surface side, a second portion continuing at said intermediate surface side, and a third portion further at said second header portion surface side, said first portion directly opposing said third portion;
   wherein said antenna device extends over said first and second header portion surface sides in parallel y-z planes and extends over said intermediate surface side in the x-z plane; and
   wherein said first portion and said portion of said antennas device are tilted in relation to the x-y plane.

2. The implantable medical device as claimed in claim 1, wherein said first portion and said third portion of said antenna device is tilted an angle within the range of 30- 60 degrees in relation to the x-y plane.

3. The implantable medical device as claimed in claim 1, wherein said antenna device is embedded in said header portion.

4. The implantable medical device as claimed in claim 1, wherein said antenna device is arranged at surfaces of said header portion.

5. The implantable medical device as claimed in claim 1, wherein said antenna device comprises a magnetic field antenna.

6. The implantable medical device as claimed in claim 5 wherein said antenna device is a closed loop antenna.

7. The implantable medical device as claimed in claim 1, wherein said antenna further includes a fourth portion on said first header portion surface having a first part that is tilted in the y-z plane in relation to x-y plane and a second part that extends generally parallel to the y axis.

* * * * *